(12) United States Patent
McLaughlin

(10) Patent No.: US 6,267,012 B1
(45) Date of Patent: Jul. 31, 2001

(54) TENSILE SPECIMEN TEST GRIP

(75) Inventor: Michael D. McLaughlin, Germantown, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/288,312

(22) Filed: Apr. 8, 1999

(51) Int. Cl.[7] .................................................. G01N 3/02
(52) U.S. Cl. ................................. 73/856; 73/859; 73/831
(58) Field of Search ...................... 73/856–860, 831–833

(56) References Cited

U.S. PATENT DOCUMENTS

| | | | |
|---|---|---|---|
| 5,297,441 | * 3/1994 | Smith et al. | 73/860 |
| 5,585,570 | * 12/1996 | Raymond | 73/856 |
| 5,798,463 | * 8/1998 | Doudican et al. | 73/789 |

* cited by examiner

Primary Examiner—Benjamin R. Fuller
Assistant Examiner—Maurice Stevens
(74) Attorney, Agent, or Firm—Jacob Shuster

(57) ABSTRACT

Tensile loading is applied to a notched specimen bar through the base of a fixture grip having a pair of interfitting pieces releasably held assembled in a fixture position in axial abutment with the base and in engagement with the specimen bar by means of a pair of fastener bolts, one of which is loosened so as to act as a hinge accommodating pivotal displacement of the interfitting pieces from the fixture position upon removal of the other fastener bolts.

2 Claims, 3 Drawing Sheets

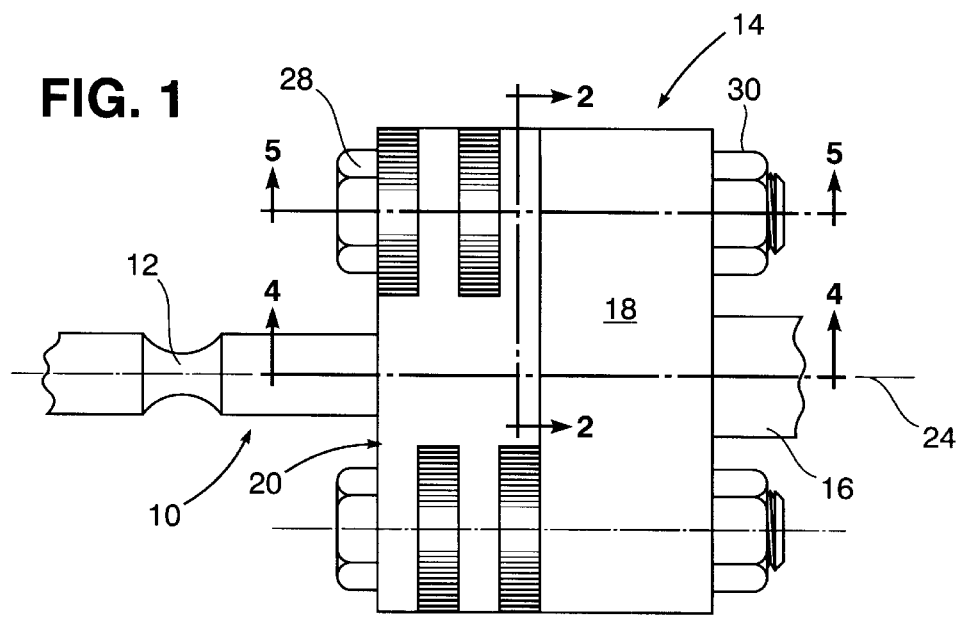
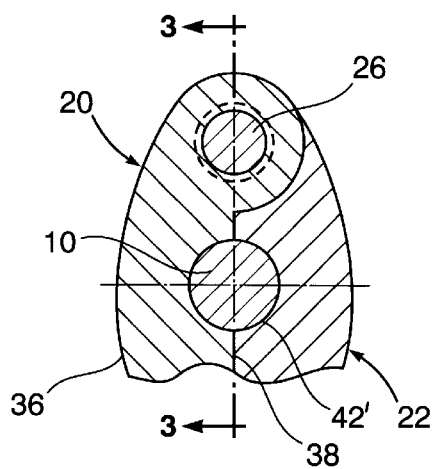
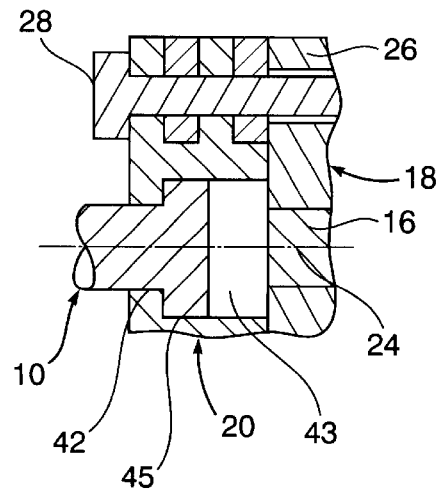

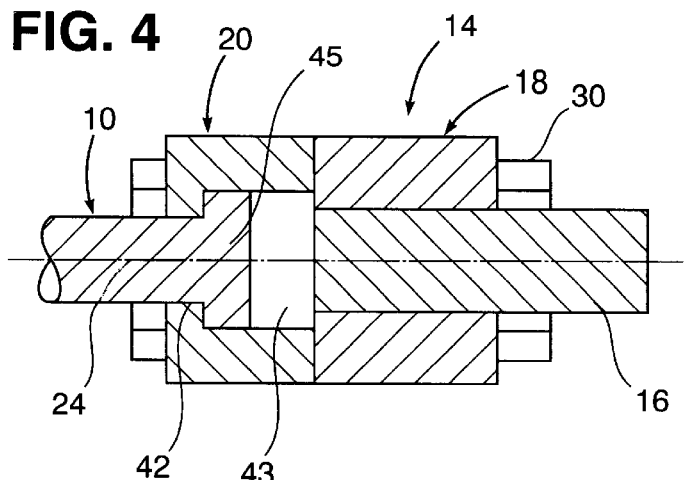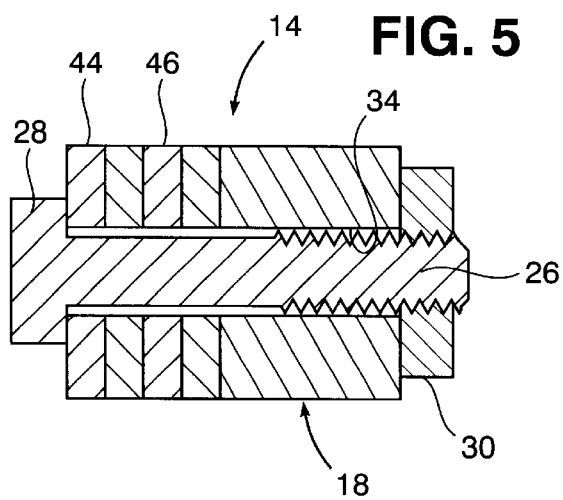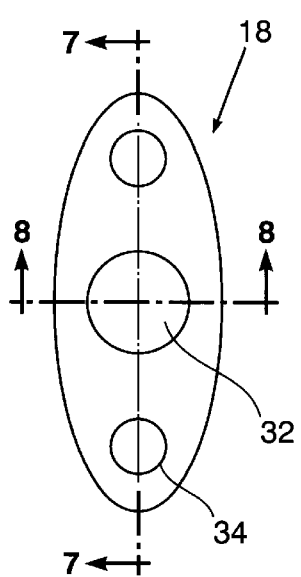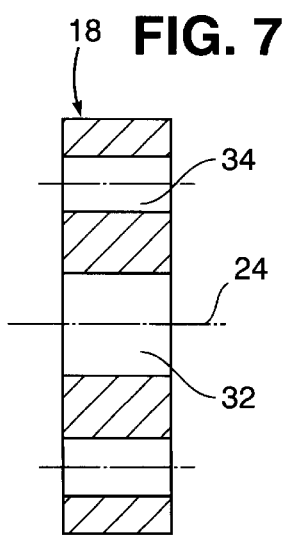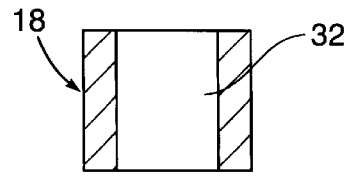

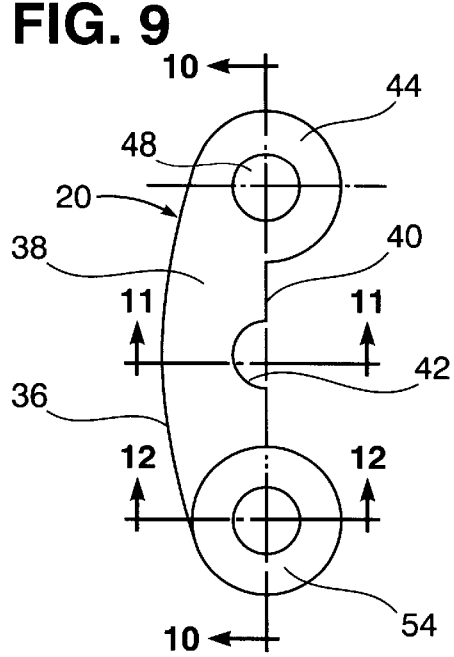
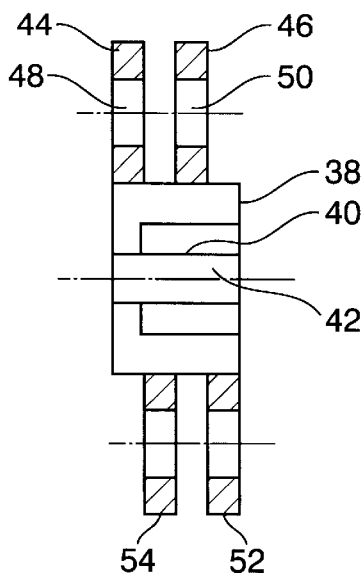
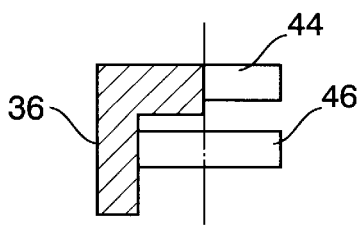
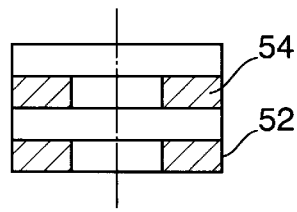
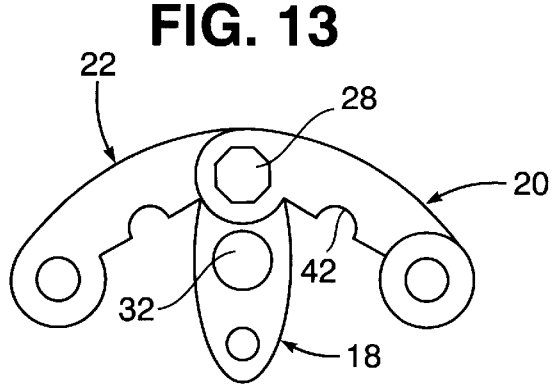

TENSILE SPECIMEN TEST GRIP

The present invention relates in general to the application of tensile load to specimens for structural testing thereof.

BACKGROUND OF THE INVENTION

Tensile specimens are subjected to dynamic testing at a high rate by attachment to and release from a testing machine through which an axial displacement is imposed on the specimen and diametrical displacement results, with both displacements being recorded. In the case of a notched cylindrical bar type of tensile specimen, cloverleaf shaped fixture grips are presently utilized for attachment to and removal of such specimens from the testing machine. Such fixture grips require complete assembly of parts during set up by means of four bolt fasteners and extensive fixturing by reason of which data recording errors are introduced during high rate dynamic testing operation because of fixture flexure. It is therefore an important object of the present invention to provide fixture grips for tensile specimen bars in dynamic test machine installations as aforementioned, which will decrease set up and removal time between tests to thereby increase the testing rate as well as to reduce flexure causing errors.

SUMMARY OF THE INVENTION

In accordance with the present invention, a hinge type of fixture grip is provided for removable attachment to each axial end of a notched bar type of tensile specimen within a dynamic test machine installation. Such grip is formed from three parts consisting of one base piece of uniform thickness in axial abutment on one planar side thereof with two interfitting hinge parts held assembled by a pair of bolt fasteners, one of which is completely removed while the other is partially loosened so as to act as a hinge pivot for pivotal displacement of the intermitted hinge parts during set up or removal of the fixture grip from the tensile specimen bar.

BRIEF DESCRIPTION OF DRAWING

A more complete appreciation of the invention and many of its attendant advantages will be readily appreciated as the same becomes better understood by reference to the following detailed description when considered in connection with the accompanying drawing wherein:

FIG. 1 is a side elevation view of one axial end portion of a notched specimen bar held fixed in a tensile testing installation by a fixture grip constructed in accordance with one embodiment of the present invention;

FIG. 2 is a partial section view taken substantially through plane indicated by section line 2—2 in FIG. 1;

FIG. 3 is a section view taken substantially through a plane indicated by section line 3—3 in FIG.2;

FIGS. 4 and 5 are section views respectively taken substantially through planes indicated by section lines 4—4 and 5—5 in FIG. 1;

FIG. 6 is a front elevation view of a disassembled base piece of the fixture grip shown in FIG. 1;

FIGS. 7 and 8 are section views respectively taken substantially through planes indicated by section lines 7—7 and 8—8 in FIG. 6;

FIG. 9 is a front elevation view of a disassembled hinge piece of the fixture grip shown in FIG. 1;

FIGS. 10, 11 and 12 are section views respectively taken substantially through planes indicated by section lines 10—10, 11—11 and 12—12 in FIG. 9; and FIG. 13 is a front elevation view of the fixture grip illustrated in FIGS. 1–12, in a hinge opened condition removed from the notched specimen bar shown in FIGS. 1–4.

DETAILED DESCRIPTION OF PREFERRED EMBODIMENT

Referring now to the drawing in detail, FIG. 1 illustrates an axially loaded tensile specimen bar 10 of a generally cylindrical shape having an intermediate notch 12 therein. Each axial end portion of the bar 10 is received within a fixture grip assembly 14 constructed in accordance with the present invention. Each grip assembly 14 is associated with a base stud 16 which is attached to a test machine (not shown) through which dynamic testing of the bar 10 as a tensile specimen is performed, including measurement of its axial extension and diametrical contraction. The structural arrangement of each grip assembly 14 at the opposite axial ends of the specimen bar 10, to which the present invention relates, minimizes flexing of the fixturing used on the bar 10 during installation within the test machine and accommodates the provision of more accurate measurement and recordation of data by such test machine.

Each grip assembly 14 as shown in FIGS. 1–5 consists of a base piece 18 attached to the test machine by stud 16 and a pair of interfitted hinge pieces 20 and 22 held in axial abutment with the base piece 1 8 while in alignment with an axis 24 of the specimen bar 10 and the stud 16. All three pieces 18, 20 and 22 of each grip assembly 14 are interconnected by a pair of threaded bolts 26 having heads 28 at one axial end respectively abutting the interfitted hinge pieces 20 and 22. Screw nuts 30 are threaded onto projecting ends of the bolts 26 for abutment with the base piece 18 as shown in FIG. 5 to hold the three pieces 18, 20 and 22 assembled.

The base piece 18 as shown in FIGS. 6–8, has parallel spaced, oval shaped planar sides perpendicular to the axis 24. A central cylindrical bore 32 is formed in the base piece 18, of a diameter substantially equal to that of the stud 16 received therethrough. A pair of cylindrical bores 34 are also formed in the base piece 18 equally spaced from the central bore 34 for receiving the bolts 26 therethrough.

Each of the intermitted pieces 20 and 22 are of similar construction. As shown in FIGS. 9–12, the hinge piece 20 is oval shaped along one side edge 36 to match one planar side of the base piece 18 with which it is in aligned abutment when attached thereto by both of the bolts 26. The other planar side of the base piece 18 is matched by one side of the other hinge piece 22. The intermediate portion 38 of the hinge piece 20 extends axially along its entire width, between side edge 36 and an edge 40 as shown in FIG. 9. A semi-circular recess 42 is formed in the edge 40. A similar recess 42' is formed in the other piece 22 abutting the edge 40 of piece 20, as shown in FIG. 2, to form a cylindrical bore through which the bar 10 extends into an enclosure 43, as shown in FIGS. 3 and 4, within which a flanged end portion 45 of the bar 10 is retained.

A pair of axially spaced extensions 44 and 46 extend radially from the intermediate portion 38 of the piece 20, having aligned openings 48 and 50 formed therein as shown in FIGS. 9, 10 and 11 for receiving one of the bolts 26 therethrough. Another pair of axially spaced extensions 52 and 54 of the piece 20 extend radially in the opposite direction from the intermediate portion 38. Such extensions 52 and 54 also have aligned openings therein as shown in FIGS. 9, 10 and 12 for receiving the other of the bolts 26 therethrough.

The grip 14 is held assembled in a fixture position as shown in FIGS. 1–5 by the two bolts 26. To disengage the grip 14 from such position in abutment with specimen bar 10, only one of the bolts 26 is removed and the other merely loosened so as to enable the hinge pieces 20 and 22 to swing apart to a disassembly position as shown in FIG. 13. Complete assembly and disassembly of the three parts 18, 20 and 22 of the grip 14 is thereby avoided so as to decrease setup and removal time between tests performed on a specimen bar 10. Also, there is a reduction in the number of parts heretofore deemed necessary to form the fixture grips performing all of the test functions associated with that of grip assembly 14 as hereinbefore described.

Obviously, other modifications and variations of the present invention may be possible in light of the foregoing teachings. It is therefore to be understood that within the scope of the appended claims the invention may be practiced otherwise than as specifically described.

What is claimed is:

1. In combination with a test specimen, a grip assembly removably attached to the test specimen in a fixture position, comprising: a base through which tensile loading is exerted on the test specimen only in the fixture position; a pair of interfitting pieces in abutment with the base; and fastener means interconnecting the base with said interfitting pieces for pivotal displacement thereof relative to the base between said fixture position in engagement with the test specimen and a release position disengaged therefrom; said fastener means comprising: two bolts extending through the base and said pair of the interfitting pieces in spaced relation to the test specimen, one of said bolts establishing a hinge axis about which said pivotal displacement of the interfitting pieces occurs from the fixture position upon removal of the other of the bolts; each of said interfitting pieces comprising: an intermediate portion having a recess engageable with the test specimen in the fixture position; and axially spaced extensions projecting radially from the intermediate portion having aligned openings through which the two bolts extend.

2. The combination as defined in claim 1 wherein said base extends in axial alignment with the test specimen between opposite planar sides in abutment with the interfitting pieces.

* * * * *